United States Patent [19]
Herbst et al.

[11] Patent Number: 5,637,222
[45] Date of Patent: Jun. 10, 1997

[54] PROCESS FOR THE FRACTIONAL SEPARATION OF (METH)ACRYLIC ACID FROM A MIXTURE CONTAINING (METH) ACRYLIC ACID

[75] Inventors: Holger Herbst, Frankenthal; Gerhard Nestler, Ludwigshafen; Ulrich Hammon, Mannheim, all of Germany

[73] Assignee: BASF Aktiengesellschaft, Ludwigshafen, Germany

[21] Appl. No.: 584,302

[22] Filed: Jan. 11, 1996

[30] Foreign Application Priority Data

Jan. 18, 1995 [DE] Germany .................. 19501325.5

[51] Int. Cl.6 .................................................. B01D 61/16
[52] U.S. Cl. .................................... 210/634; 210/651
[58] Field of Search ........................ 560/218; 210/634, 210/511, 651

[56] References Cited

U.S. PATENT DOCUMENTS

| | | |
|---|---|---|
| 2,147,306 | 2/1939 | McCulloch . |
| 4,147,721 | 4/1979 | Leacock ................... 562/532 |
| 4,166,774 | 9/1979 | Wagner ..................... 203/82 |
| 4,317,926 | 3/1982 | Sato et al. ................. 562/532 |

FOREIGN PATENT DOCUMENTS

| | | |
|---|---|---|
| 0 058 927 | 9/1982 | European Pat. Off. . |
| 0 092 097 | 10/1983 | European Pat. Off. . |
| 0 102 642 | 3/1984 | European Pat. Off. . |
| 0 253 409 | 1/1988 | European Pat. Off. . |
| 2 136 396 | 2/1973 | Germany . |
| 22 07 184 | 8/1973 | Germany . |
| 41 01 879 | 7/1992 | Germany . |
| 43 08 087 | 9/1994 | Germany . |
| 44 31 949 | 3/1995 | Germany . |
| 44 31 957 | 3/1995 | Germany . |
| 44 05 059 | 8/1995 | Germany . |
| 1 346 737 | 2/1974 | United Kingdom . |
| WO86/00236 | 1/1986 | WIPO . |

*Primary Examiner*—Frank Spear
*Attorney, Agent, or Firm*—Oblon, Spivak, McClelland, Maier & Neustadt, P.C.

[57] ABSTRACT

A process for the fractional separation of (meth)acrylic acid from a mixture containing (meth)acrylic acid, in which (meth)acrylic acid is tapped off from the rectifying column at a point above the level at which the liquid mixture containing (meth)acrylic acid enters the rectifying column, and at at least one point of the rectifying column the reflux liquid descending therein is tapped off from the rectifying column, oligomerized and/or polymerized (meth)acrylic acid present therein is separated and the reflux liquid is subsequently recycled to the rectifying column.

8 Claims, No Drawings

PROCESS FOR THE FRACTIONAL SEPARATION OF (METH)ACRYLIC ACID FROM A MIXTURE CONTAINING (METH)ACRYLIC ACID

The present invention relates to a novel process for the fractional separation of (meth)acrylic acid from a mixture containing (meth)acrylic acid, in which (meth)acrylic acid is withdrawn from the rectifying column at a point above the level at which the liquid mixture containing (meth)acrylic acid enters the rectifying column.

"(Meth)acrylic acid" is used as an abbreviation for "acrylic acid or methacrylic acid".

(Meth)acrylic acid, either as such or in the form of esters thereof, is of particular significance for the preparation of polymers for a wide variety of applications, eg for use as adhesives.

One method of obtaining (meth)acrylic acid is by catalytic gas phase oxidation of alkanes, alkanols, alkenes or alkenals containing 3 or 4 C Atoms. (Meth)acrylic acid can be produced particularly advantageously, eg, by catalytic gas phase oxidation of propene, acrolein, tert-butanol, isobutene, isobutane, isobutyraldehyde, or methacrolein.

Other conceivable starting compounds are those from which the actual $C_3/C_4$ starting compound forms as an intermediate during gas phase oxidation. The methyl ether of tert-butanol may be mentioned by way of example.

These starting gases, usually diluted with inert gases such as nitrogen, $CO_2$, saturated hydrocarbons and/or steam, are passed in admixture with oxygen at elevated temperatures (usually from 200° to 400° C.) and optionally elevated pressure over transition-metal mixed oxide catalysts (eg containing Mo, V, W and/or Fe) and converted to (meth)acrylic acid by oxidation (cf eg DE-A 4,405,059, EP-A 253,409, EP-A 92,097, DE-A 4,431,957 and DE-A 4,431,949).

Due to numerous parallel reactions and subsequent reactions occurring in the course of the catalytic gas phase oxidation and also due to the inert diluent gases to be supplementarily used there is obtained however, in catalytic gas phase oxidation, no pure (meth)acrylic acid but a reaction mixture containing substantially (meth)acrylic acid, the inert diluent gases, and by-products, from which the (meth) acrylic acid must be separated.

Apart from (meth)acrylic acid and by-products which are comparatively simple to remove and are less detrimental in subsequent use of the (meth)acrylic acid, such as acetic acid, the reaction gas mixture also contains, in particular, lower aldehydes which are closely related to (meth)acrylic acid and therefore difficultly separable therefrom, such as formaldehyde, acetaldehyde, acrolein, methacrolein, propionaldehyde, n-butyraldehyde, benzaldehyde, furfural and crotonaldehyde and also, optionally, maleic anhydride (based on the amount of (meth)acrylic acid present in the reaction mixture the total amount of these secondary components, which are frequently considerably undesirable in subsequent use, is usually <2 wt %).

The separation of (meth)acrylic acid from the reaction gas mixture is usually carried out via processes involving extraction and rectification, the (meth)acrylic acid usually being withdrawn from the rectifying column in the latter case at a point above the level at which the mixture containing (meth)acrylic acid enters the rectifying column (eg overhead withdrawal or withdrawal through a side outlet).

For example DE-A 4,436,243 relates to a process for the separation of (meth)acrylic acid from the reaction gas mixture formed in the catalytic gas phase oxidation by countercurrent absorption using a high-boiling inert hydrophobic organic liquid, in which the reaction gas mixture is fed to an absorption column countercurrently to the descending high-boiling inert hydrophobic organic liquid, a rectifying process being superimposed on the absorption process occurring naturally in the absorption column, by withdrawing from the absorption column an amount of energy exceeding its energy output occurring as a result of its contact with ambient temperature, and separating (meth)acrylic acid, by fractional distillation, from the liquid effluent from the absorption column (absorbate) containing (meth)acrylic acid and absorbent as main components and also lower aldehydes and possibly maleic anhydride as secondary components, via a side outlet (at a point above the feed point to the rectifying column). The resulting (meth)acrylic acid is designated as crude (meth)acrylic acid. It usually has a purity >98 wt %, the impurities being particularly recruted from the said lower aldehydes and any maleic anhydride, whereas the separation of (meth)acrylic acid from the high-boiling inert organic liquid absorbent takes place substantially quantitatively.

According to DE-A 4,436,243 suitable high-boiling inert hydrophobic organic liquids (absorbents) are all of those liquids whose boiling temperature is, under standard pressure (1 atm), above the boiling temperature of (meth)acrylic acid and which to an extent of at least 70 wt % consist of molecules which contain no outwardly effective polar group and which are thus, for example, not capable of forming hydrogen bridges.

DE-PS 2,136,396 and DE-A 4,308,087 also reveal that it is possible to separate acrylic acid from the reaction gas mixture from the catalytic gas phase oxidation of propylene and/or acrolein by countercurrent absorption using a high-boiling inert hydrophobic organic liquid. The process is essentially carried out by passing the reaction gas mixture through a conventional absorption column countercurrently to the descending liquid absorbent, then substantially removing the simply separable and readily volatile secondary components, in the desorption column, from the liquid effluent leaving the absorption column and substantially composed of acrylic acid, the absorbent, and secondary components, by stripping with inert gas, and subsequently treating the liquid effluent leaving the desorption column and containing acrylic acid and the absorbent as main components and also lower aldehydes and possibly maleic anhydride as secondary components by rectification in a rectifying column in order to separate crude acrylic acid as overheads.

EP-B 102,642, GB-PS 1,346,737 and DE-B 2,207,184 relate to the fractional separation of pure (meth)acrylic acid from crude (moth)acrylic acid, which is improved by adding compounds to the crude (meth)acrylic acid, which exhibit an —$NH_2$ group. The primary amines bind the aldehydes present as impurities to a great extent with the formation of high-boiling compounds, from which pure (meth)acrylic acid can be separated in a high degree of purity eg as overheads from a rectifying column.

A disadvantage of all fractional separating processes in which (meth)acrylic acid is withdrawn from the rectifying column above the position at which the mixture containing (meth)acrylic acid enters the rectifying column is that the rectifying apparatus (particularly the surface of the evaporator) becomes coated with deposit relatively quickly during fractional separation, even when supplementary use is made of polymerization inhibitors such as air, hydroquinone, hydroquinone monomethyl ether, paranitrosophenol, paramethoxyphenol, and/or phenothiazine, for which reason the rectification, which is usually carried out continuously, must be interrupted at intervals in order to remove the deposit. This is also the case when the starting mixture containing (meth)acrylic acid includes no lower aldehydes. The presence of the latter however usually intensifies the formation of deposit.

It is thus an object of the present invention to provide a novel process for the fractional separation of (meth)acrylic acid from a mixture containing (meth)acrylic acid, in which (meth)acrylic acid is withdrawn from the rectifying column above the position at which the liquid mixture containing (meth)acrylic acid enters the rectifying column and in which the formation of deposit on the rectifying apparatus (particularly on the surface of the evaporator) is reduced.

Accordingly, we have found a process for the fractional separation of (meth)acrylic acid from a mixture containing (meth)acrylic acid, in which (meth)acrylic acid is withdrawn from the rectifying column at a point above the level at which the liquid mixture containing (meth)acrylic acid enters the rectifying column, wherein at at least one point of the rectifying column the reflux liquid descending therein is withdrawn from the rectifying column, oligomerized and/or polymerized (meth)acrylic acid present therein is separated and the reflux liquid is subsequently recycled to the rectifying column.

The above procedure is the result of extensive research work, during which the following relationships have been found to exist.

First of all, we have found that free radical oligomerization and/or polymerization of (meth)acrylic acid takes place to a certain extent, despite the presence of polymerization inhibitors, progressively along the rectifying column. The resulting (meth)acrylic acid oligomers and/or polymers have a higher boiling point than (meth)acrylic acid, for which reason they accumulate toward the evaporator in the case of rectifications in which (meth)acrylic acid is withdrawn from the rectifying column at a point above the level at which the liquid mixture containing (meth)acrylic acid enters the rectifying column. In addition we have found that oligomers and/or polymers of (meth)acrylic acid have increased molecular and/or colloidal solubility in (meth)acrylic acid. Since the reflux liquid running down the rectifying column has an increasingly lower content of (meth)acrylic acid from the point of withdrawal of (meth)acrylic acid toward the evaporator, the molecular and/or colloidal solubility of the (meth)acrylic acid oligomers and/or polymers in the reflux liquid thus normally sinks as it flows toward the evaporator. Simultaneously the (meth)acrylic acid oligomers and/or polymers accumulate, as described above, in this direction and increase their degree of polymerization until their solubility in the reflux liquid is exceeded and they sediment out to form a deposit on the rectifying apparatus and adhere thereto by adsorption. The latter applies in particular to the surface of the evaporator, on which locally a particularly pronounced reduction in the content of (meth)acrylic acid occurs due to evaporation of the (meth)acrylic acid.

If the batch passed to the rectifying column contains aldehydes, resin formation caused by the aldehydes additionally occurs, particularly in the lower part of the rectifying column due to the higher temperatures prevailing at that point, which is an added factor inducing the formation of deposit.

The above statements make it clear that tapping off the reflux liquid running down the rectifying column at at least one point along the rectifying column (the process step of the invention can, of course, be applied a number of times down the length of the rectifying column) followed by separation of oligomerized and/or polymerized (meth) acrylic acid present in the tapped off reflux liquid followed by the return of the purified reflux liquid to the rectifying column significantly reduces the formation of deposit in the latter and thus causes longer on-stream times of the rectifying column.

The process of the invention is advantageously carried out in a rectifying column consisting of stripping zone and an enriching zone. That is to say, the batch to be fractionally separated is introduced preferably not at the bottom, but at an inlet located at a point along the column. The part of the rectifying column located below this inlet is designated as the stripping zone and the part of the rectifying column located above this inlet as the enriching zone. The reflux liquid running down the rectifying column is in this case advantageously tapped off directly above the inlet for the mixture entering the rectifying column (ie at the bottom of the enriching zone of the rectifying column). Recycling is then advantageously effected directly below the aforementioned inlet (ie at the upper end of the stripping zone of the rectifying column).

Possible processes for separation of the oligomerized and/or polymerized (meth)acrylic acid from the reflux liquid tapped off from the rectifying column are, in particular, the processes of ultrafiltration (nanofiltration) and/or ultracentrifugation. Both of said processes are also applicable to the fractional separation of pure (meth)acrylic acid from crude (meth)acrylic acid, since both the volumetric extension and the mass density of oligomerized and/or polymerized (meth) acrylic acid differ sufficiently from the corresponding properties of monomeric (meth)acrylic acid. The difference in the mass density is particularly due to the higher spatial requirements of the electron cloud around an unsaturated double bond (for example the mass density of polymerized acrylic acid at 25° C. and 1 atm is 1.54 g/cm$^3$ whereas the mass density of monomeric acrylic acid under identical conditions is 1.05g/cm$^3$; the difference in the mass densities in the case of (meth)acrylic acid under the conditions mentioned is 1.45 g/cm$^3$ to 1.01 g/cm$^3$; cf eg Ullmann's Encyclopedia of Industrial Chemistry, 5th Edition, 1992, VCH Verlagsgesellschaft, Weinheim pp 169 and D'ANS-LAX, Taschenbuch fuer Chemiker and Physiker, 3rd Edition, Springer Verlag, 1964 Vol. II, Organische Verbindungen). Due to the higher mass density the colloidally dissolved oligomerized and/or polymerized (meth)acrylic acid accumulates at the jacket of the ultracentrifuge and can be continuously peeled off therefrom. Of course, chromatographic processes can also be used for the separation. Another generally applicable method of separation consists in evaporating the volatile components of the withdrawn reflux liquid under reduced pressure and recycling the resulting vapor phase, as such or following condensation, to the rectifying column.

The separation, as proposed by the invention, of the oligomerized and/or polymerized (meth)acrylic acid from the reflux liquid tapped off from the rectifying column can be realized in a particularly simple and efficient manner, when the fractional process relates to the separation of (meth)acrylic acid from a mixture containing (meth)acrylic acid and an inert hydrophobic organic liquid boiling at a higher temperature than the boiling point of (meth)acrylic acid as main components and also lower aldehydes as secondary components, such as occurs eg when executing the separation of (meth)acrylic acid from the reaction gas mixture formed in catalytic gas phase oxidation by the methods described in DE-A 4,436,243, DE-PS 2,136,396 and DE-A 4,308,087. That is to say, when the batch containing (meth)acrylic acid and an inert hydrophobic organic liquid boiling at a higher temperature than the boiling point of (meth)acrylic acid as main components and also lower aldehydes as secondary components for the process of the invention has been obtained eg from the reaction gas mixtures coming from the catalytic gas phase oxidation as a liquid effluent from a countercurrent absorption followed by desorption by stripping according to DE-PS 2,136,396 or DE-A 4,308,087 or as a liquid effluent from a countercurrent absorption with superimposed rectification according to DE-A 4,436,243. By high-boiling inert hydrophobic organic liquid we mean such liquids whose boiling point under standard pressure (1 atm) is above the boiling temperature of (meth)acrylic acid and in which the solubility (percent by weight, based on the weight of the solution) of (meth)acrylic acid oligomers and/or polymers at 25° C. and 1 atm is less than in pure (meth)acrylic acid.

In particularly, these are high-boiling organic liquids such as consist, to an extent of at least 70 wt %, of molecules which do not contain any outwardly effective polar groups and are thus, for example, not capable of forming hydrogen bridges. The term embraces in a closer sense here the high-boiling organic liquid absorbents which are recommended in DE-PS 2,136,396, DE-A 4,308,087 and DE-A 4,436,243. These are substantially liquids whose boiling point under standard pressure conditions is above 160° C. The following may be mentioned by way of example only: middle oil fractions from the distillation of paraffin, diphenyl ether, diphenyl, or mixtures of the aforementioned liquids such as a mixture of 70 to 75 wt % of diphenyl ether and 25 to 30 wt % of diphenyl. Another advantageous high-boiling hydrophobic organic liquid absorbent is a mixture comprising a blend of 70 to 75 wt % of diphenyl ether and 25 to 30 wt % of diphenyl, and also, 0.1 to 25 wt % of o-dimethyl phthalate based on said blend.

In the case of methacrylic acid the gas-phase catalyzed oxidative preparation can have taken place eg starting from methacrolein, which in turn can have been obtained by gas-phase catalyzed oxidation of tert-butanol, isobutane or isobutene or by the reaction of formaldehyde with propionaldehyde by the processes described in EP-B 92,097 or EP-B 58,927. Frequently the gas-phase catalyzed oxidation of tert-butanol, isobutane, or isobutene is carried out using a catalytically active material of the general formula I

$$Mo_{12}Bi_aFe_bX_c^1X_d^2X_e^3X_f^4O_n \qquad (I),$$

in which the variables have the following meanings:
X$^1$ nickel and/or cobalt,
X$^2$ thallium, an alkali metal and/or an alkaline earth metal,
X$^3$ phosphorus, arsenic, boron, antimony, tin, cerium, lead, niobium and/or tungsten,
X$^4$ silicon, aluminum, titanium and/or zirconium,
a 0.5 to 5,
b 0.01 to 3,
c 3 to 30,
d 0.02 to 2,
e 0 to 5,
f 0 to 10 and
n an integer determined by the valence and frequency of the elements in I other than oxygen,
at temperatures ranging from 300° to 400° C. and otherwise, apart from the specific temperature profile, according to the conditions set forth in DE-A 4,023,239, the methacrolein formed is usually employed for further oxidation without intermediate purification. The gas-phase catalyzed oxidation of methacrolein may be effected, apart from the specific temperature profile, as specified in DE-A 4,132,263 at temperatures ranging from 200° to 350° C. or according to DE-A 4,132,684 at temperatures ranging from 250° to 400° C. In particular the multimetal oxide catalysts mentioned in DE-A 4,022,212 may be used.

In the case of acrylic acid the gas-phase catalyzed oxidative preparation can have taken place eg in a single stage starting from acrolein or in two stages starting from propylene via acrolein. Suitable multimetal oxide catalysts for the catalytic gas phase oxidation of propylene are, in particular, those of the general formula II

$$Mo_{12}Bi_aFe_bX_c^1X_d^2X_e^3X_f^4O_n \qquad (II),$$

in which the variables exhibit the following meanings:
X$^1$ nickel and/or cobalt,
X$^2$ thallium, an alkali metal and/or an alkaline earth metal,
X$^3$ phosphorus, arsenic, boron, antimony, tin, cerium, lead, niobium and/or tungsten,
X$^4$ silicon, aluminum, titanium and/or zirconium,
a 0.5 to 5,
b 0.01 to 3,
c 3 to 10,
d 0.02 to 2,
e 0 to 5,
f 0 to 10 and
n an integer determined by the valence and frequency of the elements other than oxygen,
and for the catalytic gas phase oxidation of acrolein particularly those of the general formula III

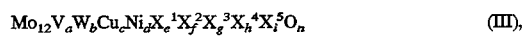

$$Mo_{12}V_aW_bCu_cNi_dX_e^1X_f^2X_g^3X_h^4X_i^5O_n \qquad (III),$$

in which the variables have the following meanings:
X$^1$ one or more alkali metals,
X$^2$ one or more alkaline earth metals,
X$^3$ chromium, manganese, cerium and/or niobium,
X$^4$ antimony and/or bismuth,
X$^5$ silicon, aluminum, titanium and/or zirconium,
a 1 to 6,
b 0.2 to 4,
c 0.5 to 6,
d 0.2 to 6,
e 0 to 2,
f 0 to 3,
g 0 to 5,
h 0 to 40,
i 0 to 40 and
n an integer determined by the valence and frequency of the elements other than oxygen.

The reaction gases of the first oxidation stage are usually passed to the second oxidation stage without intermediate purification. The reaction conditions usually employed are described in, eg, DE-A 4,431,957 and DE-A 4,431,949.

Such a mixture substantially consisting of (meth)acrylic acid and an inert hydrophobic organic liquid boiling at a higher temperature than the boiling point of (meth)acrylic acid as main components and also lower aldehydes as secondary components, as described above, usually contains from 5 to 25 wt %, in most cases from 5 to 15 wt %, of (meth)acrylic acid.

Since the fractional separation of (meth)acrylic acid is carried out so as to produce an overhead effluent or an effluent issuing from a side outlet of the rectifying column, preferably under reduced pressure (advantageously at a head pressure less than 50 mbar, usually 10 to 50 mbar, frequently 10 to 20 mbar and preferably 10 to 100 mbar, the base temperatures accordingly being usually from 100° to 230° C.) and (meth)acrylic acid oligomers and/or polymers in the high-boiling inert hydrophobic organic liquids to be used exhibit a comparatively reduced molecular and/or colloidal solubility, there is given, in the case of the fractional separation of (meth)acrylic acid from a mixture substantially consisting of (meth)acrylic acid and an inert hydrophobic organic liquid boiling at a higher temperature than the boiling point of (meth)acrylic acid as main components and also lower aldehydes as secondary components, the following simple possibility of the separation of the oligomerized and/or polymerized (meth)acrylic acid from the reflux liquid tapped off from the rectifying column, as proposed in the present invention.

The mixture including (meth)acrylic acid to be fractionally separated and the inert hydrophobic organic liquid boiling at a higher temperature than the boiling point of (meth)acrylic acid is no longer directly passed to the rectifying column consisting of stripping zone and enriching zone. But instead, the batch is first of all passed to a sojourn tank and is not passed to the rectifying column until it has sojourned in said tank for a certain period of time (advantageously 0.1 to 3 h) leaving eg via an outlet situated at the bottom of the tank (this feed point then defines the enriching and stripping zones).

Moreover, the sojourn tank is connected, eg by mounting a vapor tube thereon, with the enriching zone of the rectifying column (normally at a point directly above the lowest theoretical separating stage of the enriching zone), which produces a corresponding reduced pressure in the interposed sojourn tank. For example by installation of a collecting plate at the bottom of the enriching zone of the rectifying column the direct descent of the reflux liquid from the enriching zone of the rectifying column into the stripping zone of the rectifying column is substantially prevented, and the reflux liquid is tapped off from the rectifying column and advantageously passed to the sojourn tank via an immersed inlet pipe. Furthermore, the sojourn tank is advantageously heated such that the liquid mixture present therein is kept at the boil.

That is to say, the sojourn tank acts as an evaporator, the vapor showing an increased content of (meth)acrylic acid being passed to the enriching zone of the rectifying column and the bottoms showing a decreased content of (meth) acrylic acid being passed to the stripping zone of the rectifying column. Similarly, the sojourn tank can take the form of, for example, an autocirculation evaporator, a forced-circulation evaporator, a flash evaporator, a thin film evaporator (Sambay or Luva evaporators), or a falling-film evaporator. Of course, the "sojourn-evaporator" can be designed to have one or more stages.

The (meth)acrylic acid oligomers and/or polymers present in increased concentration in solubilized form in the reflux liquid tapped off from the rectifying column separate, as a precipitate, from the bottoms of the "sojourn-evaporator", enriched in the high-boiling hydrophobic organic solvent, in significant amounts so that the effluent from the "sojourn-evaporator" passed to the stripping zone of the rectifying column includes a reflux liquid impoverished in (meth) acrylic acid oligomers and/or polymers coming from the enriching zone of the rectifying column, which significantly reduces the formation of deposit in the stripping zone of the rectifying column thus making prolonged on-stream times of said column possible. Of course, the removal of the deposit forming in the "sojourn-evaporator" is also necessary at intervals. However, operation of the rectifying column can be maintained by switching to another "sojourn-evaporator".

A certain reduction of deposit formation in the stripping zone of the rectifying column is also caused due to the fact that the vapors transferred from the "sojourn-evaporator" to the enriching zone of the rectifying column likewise have an increased content of the lower aldehydes exhibiting boiling points comparable to that of (meth)acrylic acid, which reduces resinification thereof in the stripping zone. However, the resulting reduction in deposit formation is less pronounced.

Of course, the process of the invention is carried out in the presence of conventional amounts of conventional polymerization inhibitors. The polymerization inhibitor use is preferably phenothiazine. Normally, the polymerization inhibitors are used in amounts of 50 to 1000 ppm based on the amount of (meth)acrylic acid (by weight). Furthermore, it is advantageous, due to the inhibiting action of atmospheric oxygen on the polymerization of (meth)acrylic acid, to operate the rectifying column such that it is subjected to a stream of air passing therethrough.

Suitable rectifying columns are all commonly used types. That is to say, the rectifying column can be, eg, a plate column, a loosely packed column, or a regularly packed column. Plate columns are preferably used. Valve tray, bubble-cap tray, tunnel-cap tray, sieve tray, and dual-flow tray columns may be mentioned by way of example only. Bubble-cap trays are preferably used. The dividing line between the enriching and stripping zones of the rectifying column is advantageously situated at a point located at approximately one third of the distance from the lowest to the highest theoretical separating stage.

Of course, the process of the invention may be used in combination with other prior processes for the suppression of deposit formation.

EXAMPLES (The process was carried out in the presence of 200 ppm (based on the weight of acrylic acid) of phenothiazine acting as polymerization inhibitor).

a) A reaction gas mixture containing acrylic acid was produced by catalytic gas phase oxidation of acrolein according to Example B1 of DE-A 4,302,991. 2.1 m³/L (STP) of this reaction gas mixture were cooled to 170° C. in a gas condenser by injection of a coolant mixture comprising 57.4 wt % of diphenyl ether, 20.7 wt % of diphenyl and 20 wt % of o-dimethyl phthalate.

The still-liquid contents of the coolant were subsequently separated from the gas phase consisting of reaction gas and evaporated coolant in a separator. The gas phase exhibiting a temperature of 170° C. was fed to a bubble-cap tray column having 27 trays of a diameter of 80 mm at a point below the first tray and subjected to a countercurrent of 3 L/h of absorbent likewise composed of 57.4 wt % of diphenyl ether, 20.7 wt % of diphenyl and 20 wt % of o-dimethyl phthalate and fed to the top of the column at a temperature of 45° C. The effluent of the absorption column was indirectly heated to 105° C. in a heat exchanger and fed to the head of a desorption column designed as a bubble-cap tray column having 20 trays. In the desorption column components which are readily volatile compared with acrylic acid such as acetic acid were substantially removed from the mixture otherwise containing (acrylic acid)/(lower aldehydes)/absorbent by stripping with nitrogen (400 L/h, countercurrently). The effluent leaving the desorption column consisted of 84.5 wt % of absorbent, 15 wt % of acrylic acid and particularly lower aldehydes as secondary components.

It was passed at a temperature of 25° C. and at a rate of 3 L/h into a rectifying column including 20 bubble-cap trays and subjected to a stream of air passing therethrough (diameter of the column: 80 mm) between the fifth and sixth trays (counting from the evaporator). The rectifying column was operated at a bottom temperature of 160° C. and a bottom pressure of 130 mbar and a top pressure of 80 mbar.

60 mL of acrylic acid per hour having a purity of 99.3 wt % were continuously withdrawn through a side flue between the fifteenth and sixteenth tray (counting from the evaporator). The vaporous overheads were condensed, admixed with polymerization inhibitor and recycled to the rectifying column at a point above the top bubble-cap tray up to a rate of withdrawal of 5 mL/h.

Following an on-stream time of 165 h operation of the rectifying column had to be stopped due to excessive formation of deposit in the stripping zone of the rectifying column.

b) As a) except that the effluent leaving the desorption column was first of all passed into a heated round flask exhibiting a capacity of 500 mL, heated therein to a temperature of 150° C. and at a residence time of 0.5 h and a working volume of 250 ml passed to the rectifying column between the fifth and sixth trays (counting from the evaporator) via a bottom outlet of the round flask. Following an on-stream time of 167 h the operation of the rectifying column had to be terminated. Virtually no formation of deposit could be found on the internal surface of the sojourn round flask.

c) As b) except that the sojourn round flask was connected to the enriching zone of the rectifying column via a vapor tube situated directly above the lowest bubble-cap tray of the enriching zone. The on-stream time of the rectifying column until forced to terminate increased to 276 h. Moderate formation of deposit occurred on the internal surface of the sojourn round flask.

d) As c) except that the descent of the reflux liquid from the enriching zone of the rectifying column into the stripping zone of the rectifying column was prevented in that the lowest tray of the enriching zone was in the form of a collecting plate, from which the reflux liquid was passed to the sojourn round flask via an immersed inlet pipe.

Even after an on-stream time of 820 h still no termination of the operation of the rectifying column was necessary. A heavy deposit formed on the internal surface of the sojourn round flask.

When steady-state conditions prevailed, the content of acrylic acid in the sojourn round flask was 5 wt %, based on the weight of the liquid present therein.

We claim:

1. Process for the fractional separation of (meth)acrylic acid from a mixture containing (meth)acrylic acid, in which (meth)acrylic acid is tapped off from the rectifying column at a point above the level at which the liquid mixture containing (meth)acrylic acid enters the rectifying column, wherein at at least one point of the rectifying column the reflux liquid descending therein is tapped off from the rectifying column, oligomerized and/or polymerized (meth) acrylic acid present therein is separated and the reflux liquid is subsequently recycled to the rectifying column.

2. The process according to claim 1, wherein said mixture containing (meth)acrylic acid is obtained from the catalytic gas phase oxidation of alkanes, alkanols, alkenes or alkenals containing 3 or 4 C atoms.

3. The process according to claim 2, wherein said mixture containing (meth)acrylic acid is obtained by catalytic gas phase oxidation of propene, acrolein, tert-butanol, isobutene, isobutane, isobutyraldehyde or methacrolein.

4. The process according to claim 2, wherein the catalyst of said catalytic gas phase oxidation is of the formula I

in which the variables have the following meanings:

$X^1$ nickel and/or cobalt, $X^2$ thallium, an alkali metal and/or an alkaline earth metal, $X^3$ phosphorus, arsenic, boron, antimony, tin, cerium, lead, niobium and/or tungsten, $X^4$ silicon, aluminum, titanium and/or zirconium, a 0.5 to 5, b 0.01 to 3, c 3 to 30, d 0.02 to 2, e, 0 to 5, f 0 to 10 and n an integer determined by the valence and frequency of the elements in I other than oxygen.

5. The process according to claim 4, wherein the temperature of said gas phase oxidation is from 300° to 400° C.

6. The process according to claim 1, wherein said oligomerized and/or polymerized (meth)acrylic acid are separated by ultra filtration and/or ultracentrifugation.

7. The process according to claim 1, wherein said mixture containing (meth)acrylic acid comprises an inert hydrophobic organic liquid boiling at a higher temperature than the boiling point of (meth)acrylic acid as main components and lower aldehydes as secondary components.

8. The process according to claim 7, wherein the rectifying column comprises a stripping zone and an enriching zone at the bottom of the column, the enriching zone having a sojourn tank connected thereto, said reflux liquid being introduced into said sojourn tank before being recycled to the rectifying column.

* * * * *